(12) United States Patent
Shimada (10) Patent No.: US 11,756,176 B2
(45) Date of Patent: Sep. 12, 2023

(54) IMAGE PROCESSING APPARATUS AND CONTROL METHOD FOR SAME

(71) Applicant: CANON KABUSHIKI KAISHA, Tokyo (JP)

(72) Inventor: Tetsuo Shimada, Niigata (JP)

(73) Assignee: Canon Kabushiki Kaisha, Tokyo (JP)

( * ) Notice: Subject to any disclaimer, the term of this patent is extended or adjusted under 35 U.S.C. 154(b) by 457 days.

(21) Appl. No.: 17/130,283

(22) Filed: Dec. 22, 2020

(65) Prior Publication Data

US 2021/0150686 A1 May 20, 2021

Related U.S. Application Data

(63) Continuation of application No. PCT/JP2019/018252, filed on May 7, 2019.

(30) Foreign Application Priority Data

Jul. 9, 2018 (JP) .................................. 2018-130010

(51) Int. Cl.
*G06T 5/50* (2006.01)
*A61B 6/00* (2006.01)
(Continued)

(52) U.S. Cl.
CPC ................ *G06T 5/50* (2013.01); *A61B 6/482* (2013.01); *A61B 6/5229* (2013.01); *G06T 5/002* (2013.01);
(Continued)

(58) Field of Classification Search
CPC .. G06T 5/50; G06T 5/002; G06T 5/10; G06T 2207/20056; G06T 2207/20064;
(Continued)

(56) References Cited

U.S. PATENT DOCUMENTS

| 4,463,375 A | 7/1984 | Macovski |
| 5,301,107 A | 4/1994 | Shimura |

(Continued)

FOREIGN PATENT DOCUMENTS

| JP | S59-071740 A | 4/1984 |
| JP | H04-318775 A | 11/1992 |
| JP | H05-236351 A | 9/1993 |

OTHER PUBLICATIONS

Ping Chen et al., "Varying-energy CT imaging method based on EM-TV", Measurement Science & Technology, IOP, Bristol, GB, vol. 27, No. 11, Sep. 20, 2016, pp. 1-7.

(Continued)

*Primary Examiner* — Jose L Couso
(74) *Attorney, Agent, or Firm* — Venable LLP (57) ABSTRACT

An image processing apparatus comprises an obtaining unit that obtains a plurality of images obtained by irradiating radiation having different energies, a generating unit that generates a processed image by compositing the plurality of images, and a compositing unit that generates a composite image by compositing one image among the plurality of images and the processed image so as to enhance a low-frequency component of the one image and enhance a high-frequency component of the processed image.

17 Claims, 8 Drawing Sheets

(51) Int. Cl.
*G06T 5/00* (2006.01)
*G06T 5/10* (2006.01)

(52) U.S. Cl.
CPC ...... *G06T 5/10* (2013.01); *G06T 2207/20056* (2013.01); *G06T 2207/20064* (2013.01); *G06T 2207/20221* (2013.01); *G06T 2207/30004* (2013.01)

(58) Field of Classification Search
CPC . G06T 2207/20221; G06T 2207/30004; G06T 2207/10116; G06T 2207/20192; G06T 5/001; G06T 5/004; G06T 2207/10081; G06T 2207/20016; G06T 11/005; G06T 2207/30068; G06T 2207/30096; G06T 5/20; G06T 7/0014; A61B 6/482; A61B 6/5229; A61B 6/5235; A61B 6/502; A61B 6/5205; A61B 6/025; A61B 6/032; A61B 6/466; A61B 6/54; H04N 5/32; H04N 5/208; H04N 1/3935; H04N 1/409; H04N 5/21; G01T 1/1647; G06V 10/8035; G06V 30/1918; G06K 9/6288
See application file for complete search history.

(56) References Cited

U.S. PATENT DOCUMENTS

| | | |
|---|---|---|
| 5,402,338 A | 3/1995 | Ito |
| 10,092,264 B2 | 10/2018 | Machida et al. |
| 10,702,234 B2 * | 7/2020 | Jain ........................ A61B 6/405 |
| 2010/0142792 A1 * | 6/2010 | Sakaguchi ............... A61B 6/03 382/128 |
| 2010/0166277 A1 | 7/2010 | Raupach |
| 2011/0050701 A1 * | 3/2011 | Toyoda ..................... G06T 3/40 382/199 |
| 2011/0206293 A1 * | 8/2011 | Sasaki ....................... G06T 5/50 382/274 |
| 2012/0063662 A1 * | 3/2012 | Kwon ..................... G06T 5/009 382/132 |
| 2013/0148871 A1 | 6/2013 | Kwon et al. |
| 2014/0044375 A1 * | 2/2014 | Xu ........................... G06T 5/002 382/260 |
| 2014/0119668 A1 | 5/2014 | Kwon et al. |
| 2014/0193095 A1 * | 7/2014 | Choe ....................... G06T 5/002 382/274 |
| 2018/0055459 A1 * | 3/2018 | Fukuda ................. A61B 6/5205 |
| 2018/0068442 A1 * | 3/2018 | Kawamura ........... G06T 7/0012 |

OTHER PUBLICATIONS

Feb. 24, 2022 European Search Report in European Patent Appln. No. 19834384.0.
Jul. 30, 2019 International Search Report in International Patent Appln. No. PCT/JP2019/018252.

\* cited by examiner

IMAGE PROCESSING APPARATUS AND CONTROL METHOD FOR SAME

CROSS-REFERENCE TO RELATED APPLICATIONS

This application is a Continuation of International Patent Application No. PCT/JP2019/018252, filed May 7, 2019, which claims the benefit of Japanese Patent Application No. 2018-130010, filed Jul. 9, 2018, both of which are hereby incorporated by reference herein in their entirety.

BACKGROUND OF THE INVENTION

Field of the Invention

The present invention relates to an image processing apparatus that processes a radiographic image, and to a control method for the same.

Background Art

An image capturing technique known as time-resolved spectral imaging is generally known. In time-resolved spectral imaging, a subject is irradiated with multiple radiation beams having different average energies in a short period of time, and the percentages of the radiation of the respective average energies transmitted through the subject to a radiation measurement surface is measured to distinguish the constituent matters of the subject. Such time-resolved spectral imaging is also used to generate radiographic images for medical applications.

CITATION LIST

Patent Literature

PTL1: Japanese Patent Laid-Open No 05-236351
In time-resolved spectral imaging, it is necessary to capture multiple images of the same area in a short period of time. Images of the same area are therefore repeatedly captured at the same dosage as when capturing images normally, which increases the exposure dose for the examinee. Although the number of images needed differs depending on the purpose for which the matters are distinguished, time-resolved spectral imaging requires a minimum of two images, and the examinee's radiation exposure dose will simply increase with each additional image that is captured. It is therefore conceivable to suppress the radiation exposure dose for the examinee by reducing the amount of radiation to suppress the radiation exposure dose per image. However, reducing the radiation dose increases the intensity of the noise and reduces the quality of each image.

PTL1 proposes performing a smoothing process on intermediate generated images for the purpose of noise reduction in dual-energy images used to create a bone-removed image in chest radiography. However, with PTL1, a large difference cannot be achieved between the radiation energies of multiple collected images, which makes it difficult to generate a favorable image from spectral imaging.

SUMMARY OF THE INVENTION

The present invention provides a technique that reduces noise in an image while suppressing a radiation exposure dose to an examinee when capturing a plurality of radiographic images.

According to one aspect of the present invention, there is provided an image processing apparatus comprising: an obtaining unit configured to obtain a plurality of images obtained by irradiating radiation having different energies; a generating unit configured to generate a processed image by compositing the plurality of images; and a compositing unit configured to generate a composite image by compositing one image among the plurality of images and the processed image so as to enhance a low-frequency component of the one image and enhance a high-frequency component of the processed image.

According to another aspect of the present invention, there is provided a control method of an image processing apparatus, the method comprising: obtaining a plurality of images obtained by irradiating radiation having different energies; generating a processed image by compositing the plurality of images; and generating a composite image by compositing one image among the plurality of images and the processed image so as to enhance a low-frequency component of the one image and enhance a high-frequency component of the processed image.

According to another aspect of the present invention, there is provided a non-transitory computer-readable storage medium storing a program that causes a computer to execute a control method of an image processing apparatus, the method comprising: obtaining a plurality of images obtained by irradiating radiation having different energies; generating a processed image by compositing the plurality of images; and generating a composite image by compositing one image among the plurality of images and the processed image so as to enhance a low-frequency component of the one image and enhance a high-frequency component of the processed image.

Further features of the present invention will become apparent from the following description of exemplary embodiments with reference to the attached drawings.

DESCRIPTION OF THE EMBODIMENTS

Embodiments of the present invention will be described hereinafter with reference to the appended drawings. In the following embodiments, the term "radiation" may include, for example, α rays, β rays, γ rays, particle rays, cosmic rays, and the like in addition to X-rays.

First Embodiment

At present, radiation imaging apparatuses using flat panel detectors (abbreviated as "FPDs" hereinafter) formed from semiconductor materials are widely used as image capturing devices for medical diagnostic imaging, non-destructive examinations, and the like using radiation. Such radiation imaging apparatuses are used, for example, in medical diagnostic imaging, as digital image capturing devices which capture still images as in general radiography, moving images as in fluoroscopy, and the like. Typically, with FPDs, integration type sensors, which measure the total amount of charge generated by the incident radiation quanta, are used to detect radiation. Noise arising in the image at this time is caused by quantum noise produced by fluctuations in the amount of photons and electrical noise produced by electric circuits/electronic circuits used to read signals.

When performing time-resolved spectral imaging, it is necessary to capture consecutive images of the same area in an extremely short period of time. To suppress quantum noise to the same strength as in normal imaging, it is necessary to emit a radiation dose equivalent to that of normal imaging for each of the consecutive images, and the radiation exposure dose to the examinee therefore rises in proportion to the number of images taken. Incidentally, because radiation having a different average energy is emitted for each of the consecutive images which are captured, the transmittance of the radiation in the subject differs depending on the matter, and each image will therefore have a different contrast. However, because the images are captured over a short period of time, the shape of the subject in the images is nearly identical. In the present embodiment, this fact (that the shape of the subject is the same between a plurality of images) is used to create an image in which the effect of noise is suppressed while suppressing the radiation exposure dose to the examinee. A radiation imaging system according to the embodiment will be described below.

Figure 1:
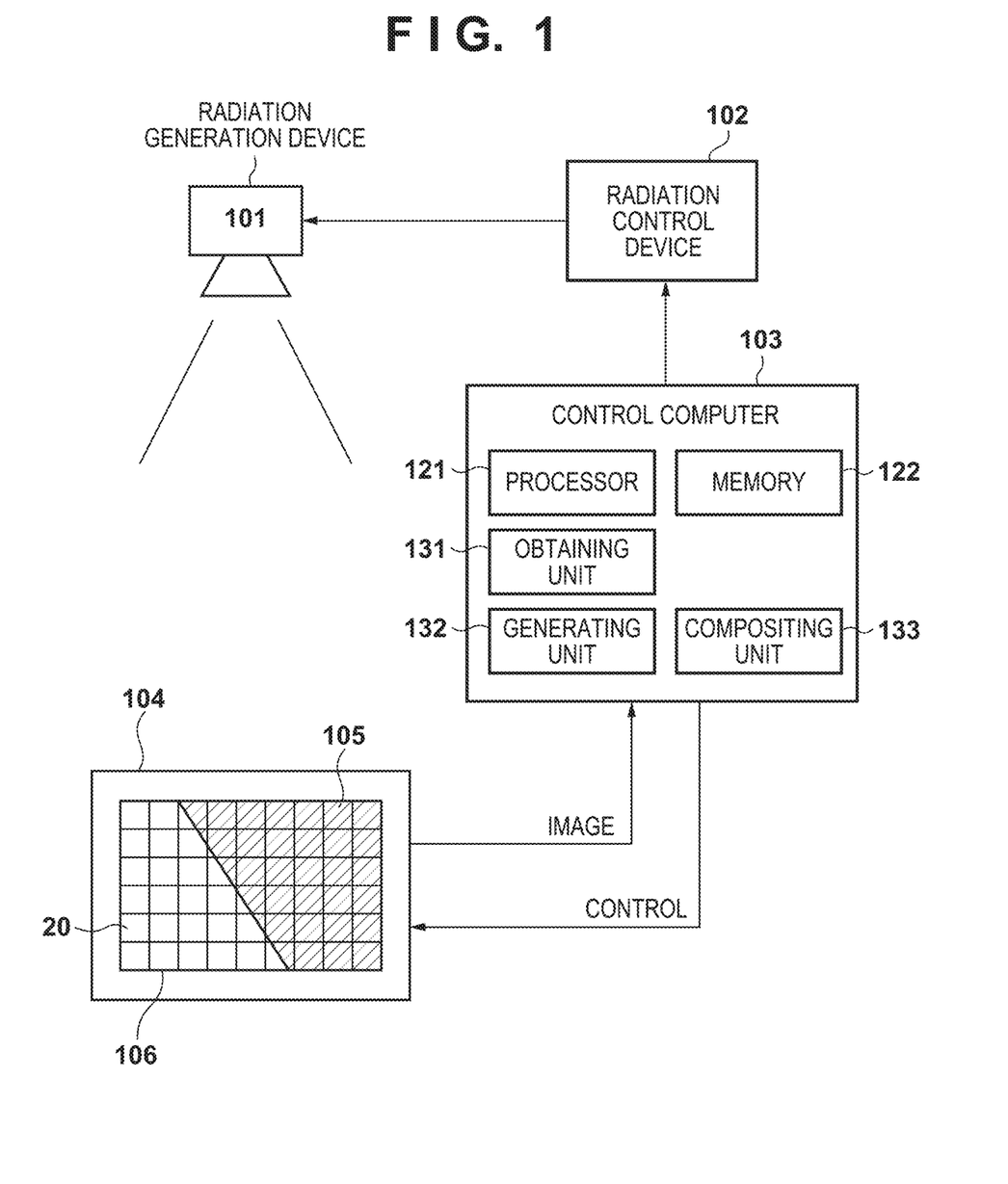
FIG. 1 is a diagram illustrating an example of the overall configuration of a radiation imaging system according to an embodiment.

FIG. 1 is a block diagram illustrating the configuration of a radiation imaging system according to a first embodiment. The radiation imaging system according to the present embodiment includes a radiation generation device 101, a radiation control device 102, a control computer 103, and a radiation imaging apparatus 104. The radiation generation device 101 generates radiation under the control of the radiation control device 102. The control computer 103 performs various types of processing by a processor 121 executing programs stored in memory 122. For example, the control computer 103 performs various types of control pertaining to radiography, image processing for spectral imaging, and so on. An obtaining unit 131, a generating unit 132, and a compositing unit 133 will be described later. The radiation imaging apparatus 104 includes a phosphor 105 that converts radiation into visible light and a two-dimensional detector 106 that detects the visible light. The two-dimensional detector 106 is a sensor in which pixels 20 that detect radiation quanta are disposed in an array of X columns×Y rows, and detects image information.

Figure 2:
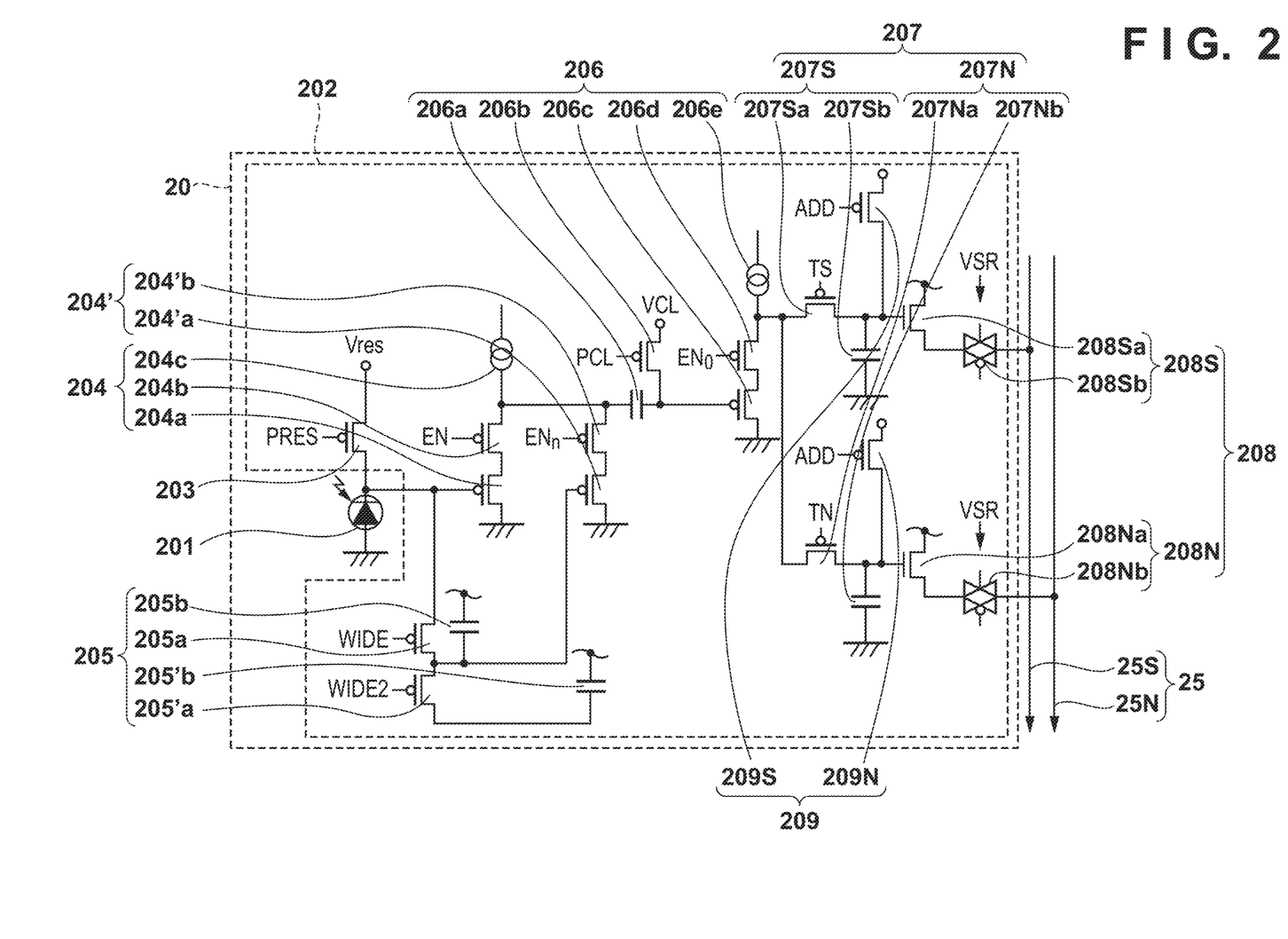
FIG. 2 is an equivalent circuit diagram illustrating a pixel in a radiation imaging apparatus according to an embodiment.

FIG. 2 is an equivalent circuit diagram of the pixel 20. The pixel 20 includes a photoelectric conversion element 201 and an output circuit unit 202. The photoelectric conversion element 201 can typically be a photodiode. The output circuit unit 202 includes an amplifier circuit unit 204, a clamp circuit unit 206, a sample hold circuit unit 207, and a selection circuit unit 208.

The photoelectric conversion element 201 includes a charge accumulating unit, and the charge accumulating unit is connected to a gate of a MOS transistor 204a of the amplifier circuit unit 204. A source of the MOS transistor 204a is connected to a current source 204c via a MOS transistor 204b. A source-follower circuit is constituted by the MOS transistor 204a and the current source 204c. The MOS transistor 204b is an enable switch that turns on when an enable signal EN supplied to the gate goes to an active level and puts the source-follower circuit into an operational state.

In the example illustrated in FIG. 2, the charge accumulating unit of the photoelectric conversion element 201 and the gate of the MOS transistor 204a constitute a common node, and this node functions as a charge-voltage conversion unit that converts the charge accumulated in the charge accumulating unit into a voltage. A voltage $V (=Q/C)$, which is determined by a charge Q accumulated in the charge accumulating unit and a capacitance value C of the charge-voltage conversion unit, arises in the charge-voltage conversion unit. The charge-voltage conversion unit is connected to a reset potential Vres via a reset switch 203. When a reset signal PRES goes to the active level, the reset switch 203 turns on, and a potential of the charge-voltage conversion unit is reset to the reset potential Vres.

The clamp circuit unit 206 uses a clamp capacitor 206a to clamp noise output by the amplifier circuit unit 204 according to the potential of the charge-voltage conversion unit which has been reset. In other words, the clamp circuit unit 206 is a circuit for canceling the aforementioned noise from the signal output from the source-follower circuit in accordance with the charge generated through the photoelectric conversion performed by the photoelectric conversion element 201. This noise includes kTC noise at the time of the reset. Clamping is done by setting a clamp signal PCL to the active level and putting a MOS transistor 206b into an on state, and then setting the clamp signal PCL to an inactive level and putting the MOS transistor 206b into an off state. The output side of the clamp capacitor 206a is connected to a gate of a MOS transistor 206c. A source of the MOS transistor 206c is connected to a current source 206e via a MOS transistor 206d. A source-follower circuit is constituted by the MOS transistor 206c and the current source 206e. The MOS transistor 206d is an enable switch that turns on when an enable signal ENO supplied to the gate goes to an active level and puts the source-follower circuit into an operational state.

A signal output from the clamp circuit unit 206 in accordance with the charge produced through the photoelectric conversion by the photoelectric conversion element 201 is written, as an optical signal, to a capacitor 207Sb via a switch 207Sa when an optical signal sampling signal TS goes to the active level. The signal output from the clamp circuit unit 206 when the MOS transistor 206b has turned on immediately after the potential of the charge-voltage conversion unit has been reset is a clamp voltage. The clamp voltage is written, as noise, into a capacitor 207Nb via a switch 207Na in response to a noise sampling signal TN going to the active level. This noise includes an offset component of the clamp circuit unit 206. A signal sample hold circuit 207S is constituted by the switch 207Sa and the capacitor 207Sb, and a noise sample hold circuit 207N is constituted by the switch 207Na and the capacitor 207Nb. The sample hold circuit unit 207 includes the signal sample hold circuit 207S and the noise sample hold circuit 207N.

When a drive circuit unit drives a row selection signal to the active level, the signal (optical signal) held in the capacitor 207Sb is output to a signal line 21S via a MOS transistor 208Sa and a row selection switch 208Sb. At the same time, the signal (noise) held in the capacitor 207Nb is output to a signal line 21N via a MOS transistor 208Na and a row selection switch 208Nb. Along with a constant current source (not shown) provided in the signal line 21S, the MOS transistor 208Sa constitutes a source-follower circuit. Likewise, along with a constant current source (not shown) provided in the signal line 21N, the MOS transistor 208Na constitutes a source-follower circuit. A signal selection circuit unit 208S is constituted by the MOS transistor 208Sa and the row selection switch 208Sb, and a noise selection circuit unit 208N is constituted by the MOS transistor 208Na and the row selection switch 208Nb. The selection circuit unit 208 includes the signal selection circuit unit 208S and the noise selection circuit unit 208N.

Each pixel 20 may include an adding switch 209S that adds the optical signals of a plurality of adjacent ones of the pixels 20. In an additive mode, an additive mode signal ADD goes to active level and the adding switch 209S turns on. This causes the capacitors 207Sb of the adjacent pixels 20 to be connected to each other by the adding switch 209S, which averages the optical signals. Likewise, each pixel 20 may include an adding switch 209N that adds the noise of a plurality of adjacent ones of the pixels 20. When the adding switch 209N turns on, the capacitors 207Nb of the adjacent pixels 20 are connected to each other by the add switch 209N, which averages the noise. An adding unit 209 includes the adding switch 209S and the adding switch 209N.

The pixel 20 may also include a sensitivity changing unit 205 for changing a sensitivity. The pixel 20 can include, for example, a first sensitivity changing switch 205a and a second sensitivity changing switch 205'a, along with circuit elements associated therewith. When a first changing signal WIDE goes to the active level, the first sensitivity changing switch 205a turns on, and a capacity value of the charge-voltage conversion unit is added to a capacity value of a first additional capacitor 205b. The sensitivity of the pixel 20 drops as a result. When a second changing signal WIDE2 goes to the active level, the second sensitivity changing switch 205'a turns on, and the capacity value of the charge-voltage conversion unit is added to a capacity value of a second additional capacitor 205'b. The sensitivity of the pixel 20 drops further as a result. By adding a function for reducing the sensitivity of the pixel 20 in this manner, a larger amount of light can be received and the dynamic range can be increased. When the first changing signal WIDE goes to the active level, an enable signal ENw may be set to the active level to cause a MOS transistor 204'a to function as a source-follower instead of the MOS transistor 204a.

The radiation imaging apparatus 104 reads out the output of the pixel circuitry described above, converts the output to digital values using an AD converter, which is not shown, and then transfers an image to the control computer 103.

Figure 3:
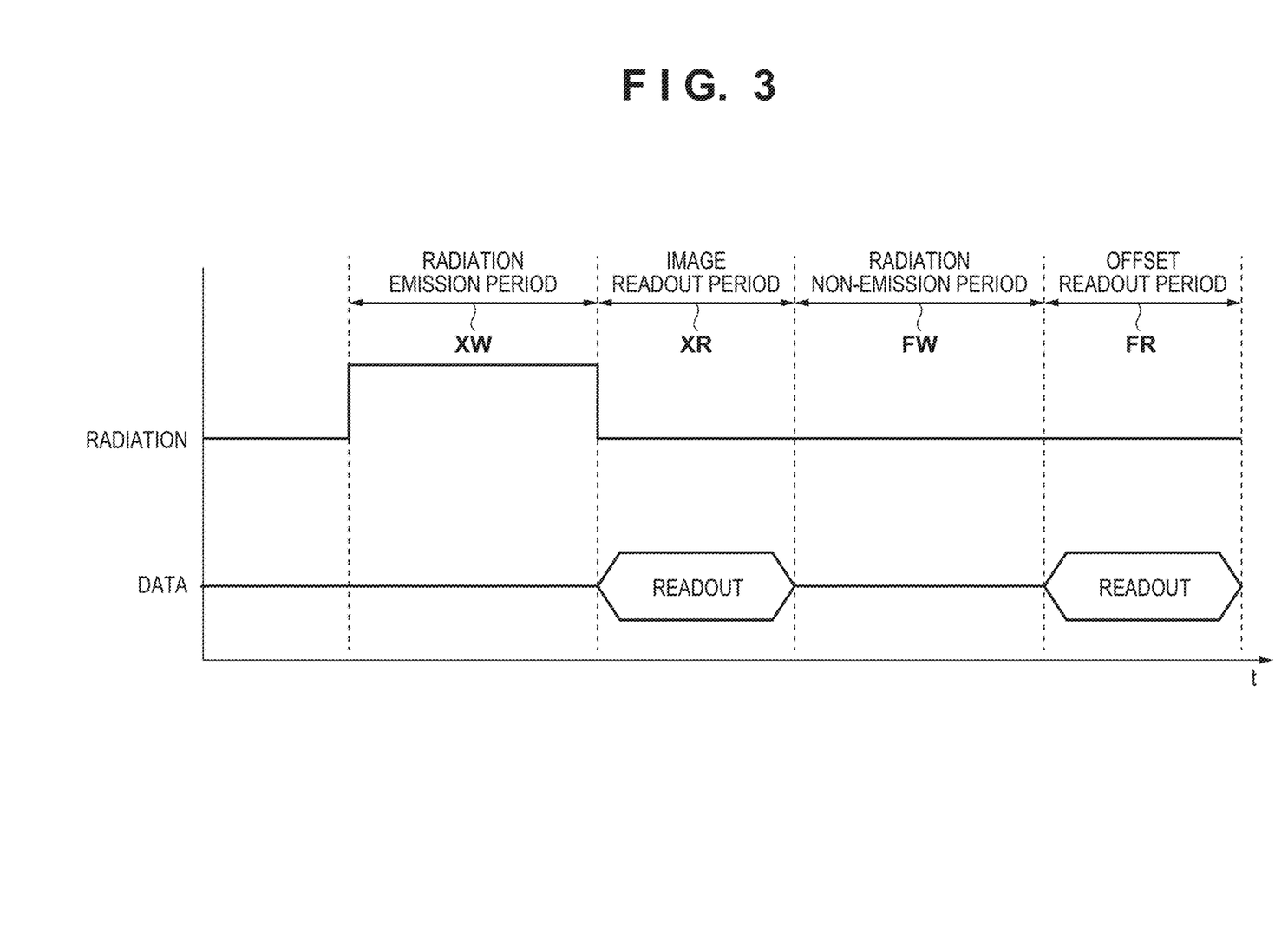
FIG. 3 is a timing chart of radiography operations.

Driving of the radiation imaging system according to the present embodiment will be described next. FIG. 3 is a timing chart of radiography operations according to the present embodiment. The waveforms in the drawing represent a radiation emission period and a data readout period, with the horizontal axis representing time. The radiation imaging system according to the present embodiment obtains a still image or a moving image with a radiation emission period (XW), an image readout period (XR), a radiation non-emission period (FW), and an offset readout period (FR) as a single frame. In the image readout period (XR), information of the charges accumulated in the pixels 20 is sequentially transferred to the control computer 103. Furthermore, unnecessary offset information is corrected by subtracting signal values obtained in the image readout period (XR) from the signal values obtained in the offset readout period (FR).

Figure 4:
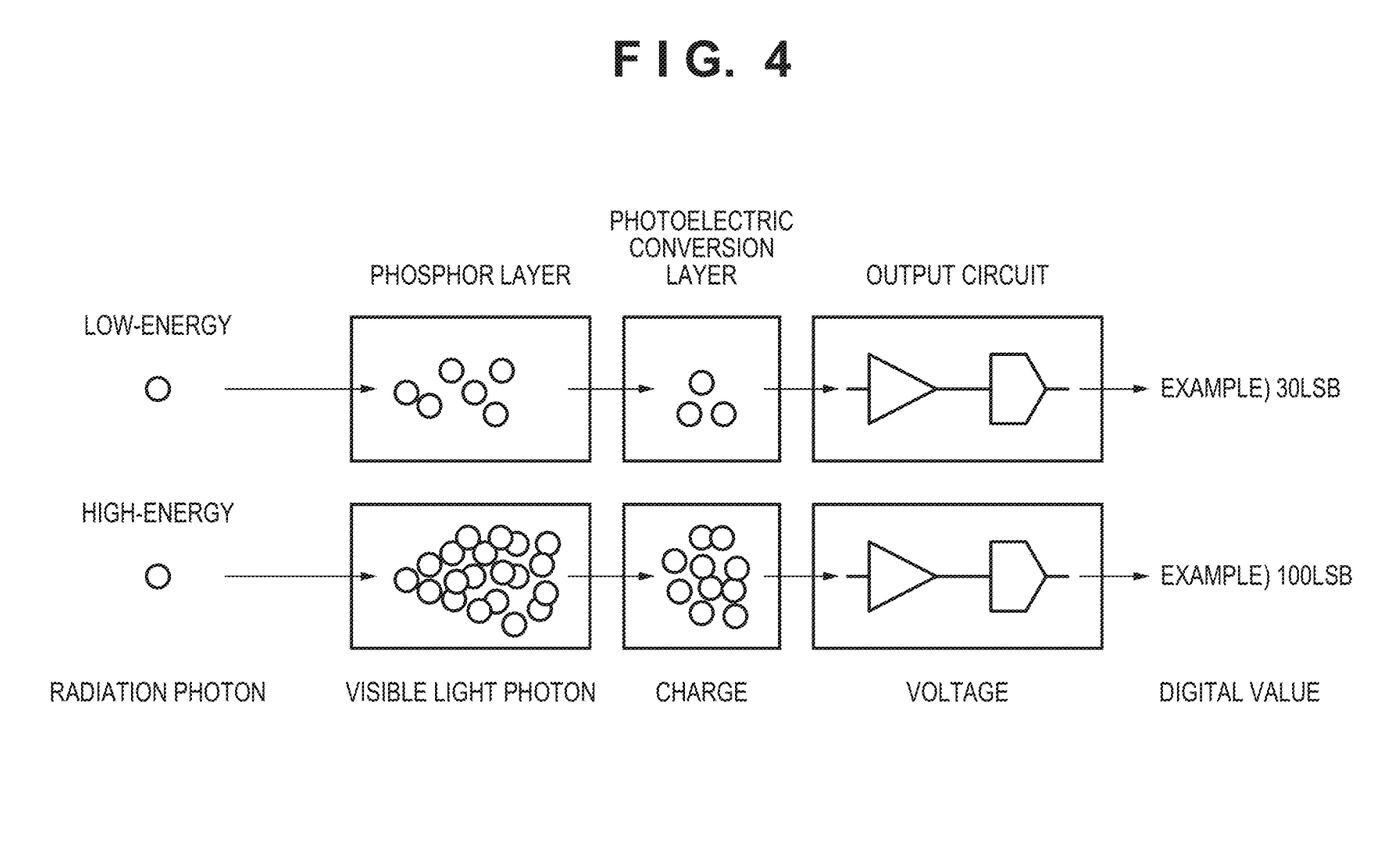
FIG. 4 is a diagram illustrating a relationship between radiation photon energy and sensor output.

FIG. 4 is a diagram illustrating a relationship between radiation photon energy and sensor output according to the present embodiment. The radiation imaging apparatus 104 includes a phosphor layer (the phosphor 105) that converts radiation into visible light photons, a photoelectric conversion layer (the two-dimensional detector 106) that converts the visible light photons into electric charges, and an output circuit that furthermore converts the charges into a voltage to obtain a digital value. When the radiation photons are absorbed by the phosphor layer, visible light photons are produced within the phosphor layer. The number of visible light photons produced at this time changes depending on the energy of the radiation photons absorbed by the phosphor layer. Specifically, more visible light photons are produced as the energy increases. Additionally, the number of charges which are produced in the photoelectric conversion layer is determined by the number of visible light photons. As such, the digital value that is ultimately output is a digital value obtained by converting this charge amount into a voltage.

To capture an image through spectral imaging, a plurality of images are obtained by irradiating the radiation imaging apparatus 104 with radiation. Here, it is assumed that a plurality of shots are taken in a short period of time to obtain the plurality of images, and that the subject does not move during this time. In this case, assuming the subject is uniform, any desired range containing a plurality of pixels is selected. Upon doing so, the pixel values will ideally be constant, but in reality, the pixel values will vary. This variation includes electrical noise (also called "system noise") and quantum noise produced by fluctuations in the number of radiation photons reaching the phosphor screen, as described above. The following will ignore the system noise to simplify the descriptions.

Quantum noise is estimated by a Poisson distribution for the number of visible light photons produced by radiation photons that reach the phosphor layer and are absorbed. A Poisson distribution with a mean value of A will also have a variance of A. If electrical noise in an offset signal is ignored, when the mean value is half A/2, the variance is also A/2, resulting in an increase of a factor of √2 in the signal strength of a noise component and a decrease in image quality. According to the Poisson distribution, a quantum noise ratio R1 when the number of visible light photons is A and A/2 (=[strength of quantum noise at visible light photon number A]:[strength of quantum noise at visible light photon number A/2]) can be calculated through [Equation 1] below.

$$R1 = \frac{\sqrt{A}}{A} : \frac{\sqrt{\frac{A}{2}}}{\frac{A}{2}} = \sqrt{A} : 2\sqrt{\frac{A}{2}} = \sqrt{A} : \sqrt{2A} = 1 : \sqrt{2}$$

[Equation 1]

Likewise, when the number of visible light photons is ⅓ of A/3, the distribution is also A/3, and the strength of the quantum noise increases by a factor of √3.

Therefore, if the strength of quantum noise in the images used in spectral imaging is to be approximately equal to that of a normal single shot, it is necessary that the number of visible light photons emitted by the phosphor per single shot be approximately equal to that of a normal single shot. As a result, when N (N>1) images are required for the spectral imaging calculations, although there will be a change in a radiation absorption coefficient due to differences in the average energy of the radiation, the radiation exposure dose will simply increase by a factor of N. Accordingly, if the number of visible light photons produced in the phosphor layer is set to 1/N with the goal of reducing the radiation exposure dose to a dose equivalent to that from a single normal shot, the quantum noise per image will be a factor of $\sqrt{N}$. In other words, although the radiation exposure dose is reduced, the image quality drops, and the calculation accuracy of the spectral imaging is reduced as well.

Here, the capturing of the plurality of images of the same area for the purpose of spectral imaging calculations is performed in an extremely short period of time. As such, it should be noted that although the signal strength of the image is affected by the types, total amounts, and proportions of the constituent matters of the subject projected at pixel locations in accordance with the different average energies of the emitted radiation, the shape of the projected subject will remain almost unchanged.

Consider noise when a plurality of digital values obtained by capturing an image of the same area in a short period of time are all used to create a single image. For example, if two images are captured in a short period of time (simultaneously) with the number of visible light photons in a single instance of capturing simply being B, the number of visible light photons will be doubled to 2B. Note that the images in which all the digital values of a plurality of images are to be used may be obtained by simply adding the plurality of images together, or weighted addition may be performed by taking into account differences in the digital values of the entire image or a part of an image of interest. Here, a ratio R2 of the quantum noise when the number of visible light photons is double B, i.e., 2B (=the strength of the quantum noise at the visible light photon number B:the strength of the quantum noise at the visible light photon number 2B) is calculated through the following [Equation 2].

$$R2 = \frac{\sqrt{B}}{B} : \frac{\sqrt{2B}}{2B} = \sqrt{B} : \frac{1}{2}\sqrt{2B} = \sqrt{B} : \sqrt{\frac{B}{2}} = 1 : \frac{1}{\sqrt{2}}$$ [Equation 2]

Assuming that differences in the strengths of the digital values from image to image is negligible, the quantum noise contained in the image is reduced to $1/\sqrt{2}$ if two images are simply added together. Likewise, if three images are added together, the strength of the quantum noise is reduced to $1/\sqrt{3}$.

At this time, the quantum noise rarely fluctuates significantly, and is produced separately in units of each pixel within the components that constitute the image. Accordingly, the quantum noise has less of an effect on low-frequency components of an image and more of an effect on the high-frequency component side. In addition, because the structure of the subject captured in the image is larger than that of the pixel unit, a contrast component thereof is generated more on the low-frequency component side than on the quantum noise side.

Based on the above considerations, the control computer 103 (the obtaining unit 131, the generating unit 132, and the compositing unit 133) according to the present embodiment performs processing so as to balance the suppression of the radiation exposure dose with the suppression of quantum noise when capturing a plurality of images. The obtaining unit 131 obtains a plurality of images obtained by emitting radiation of different energies (e.g., average energies) from the radiation imaging apparatus 104. Note that the configuration may be such that the images obtained by the radiation imaging apparatus 104 are first stored in a storage device, which is not shown, and in this case, the obtaining unit 131 may obtain a plurality of images from the storage device. The generating unit 132 generates a processed image by compositing the plurality of obtained images. For example, the generating unit 132 performs compositing processing through which a processed image having reduced quantum noise is obtained. As described above, the processing of adding together a plurality of images is an example of the compositing processing that reduces quantum noise. The compositing unit 133 generates a composite image by compositing one image among the plurality of images with the processed image so that the low-frequency component of the one image is emphasized and the high-frequency component of the processed image is emphasized. The contrast of each image in the composite image is maintained while reducing the radiation dose required to capture the plurality of images. A specific example of the processing performed by the generating unit 132 and the compositing unit 133 will be described in more detail below.

The present embodiment will describe a configuration in which two images, a low-energy image and a high-energy image, are obtained as the plurality of images. The generating unit 132 creates the processed image having reduced quantum noise by adding or averaging the digital values of the low-energy image and the high-energy image. The compositing unit 133 converts the processed image into a frequency component and extracts a high-frequency part, and converts the low-energy image and the high-energy image into frequency components and extracts respective low-frequency parts. The compositing unit 133 composites the high-frequency part of the processed image with the low-frequency part of the low-energy image, and performs an inverse frequency transform to obtain a real space image. In this manner, a low-energy image in which quantum noise is reduced and the contrast is maintained is generated. Likewise, the compositing unit 133 composites the high-frequency part of the processed image with the low-frequency part of the high-energy image, and performs an inverse frequency transform to obtain a real space image. In this manner, a high-energy image in which quantum noise is reduced and the contrast is maintained is generated. Note that when compositing the high-frequency part and the low-frequency part, it is preferable to perform the compositing so that there are no gaps in the parts.

A more specific example of the processing described above is illustrated in the flowchart of FIG. 5. Here, an example of generating a spectral imaging image from two images having different average energies of radiation photons (the low-energy image and the high-energy image) will be described.

Figure 5:
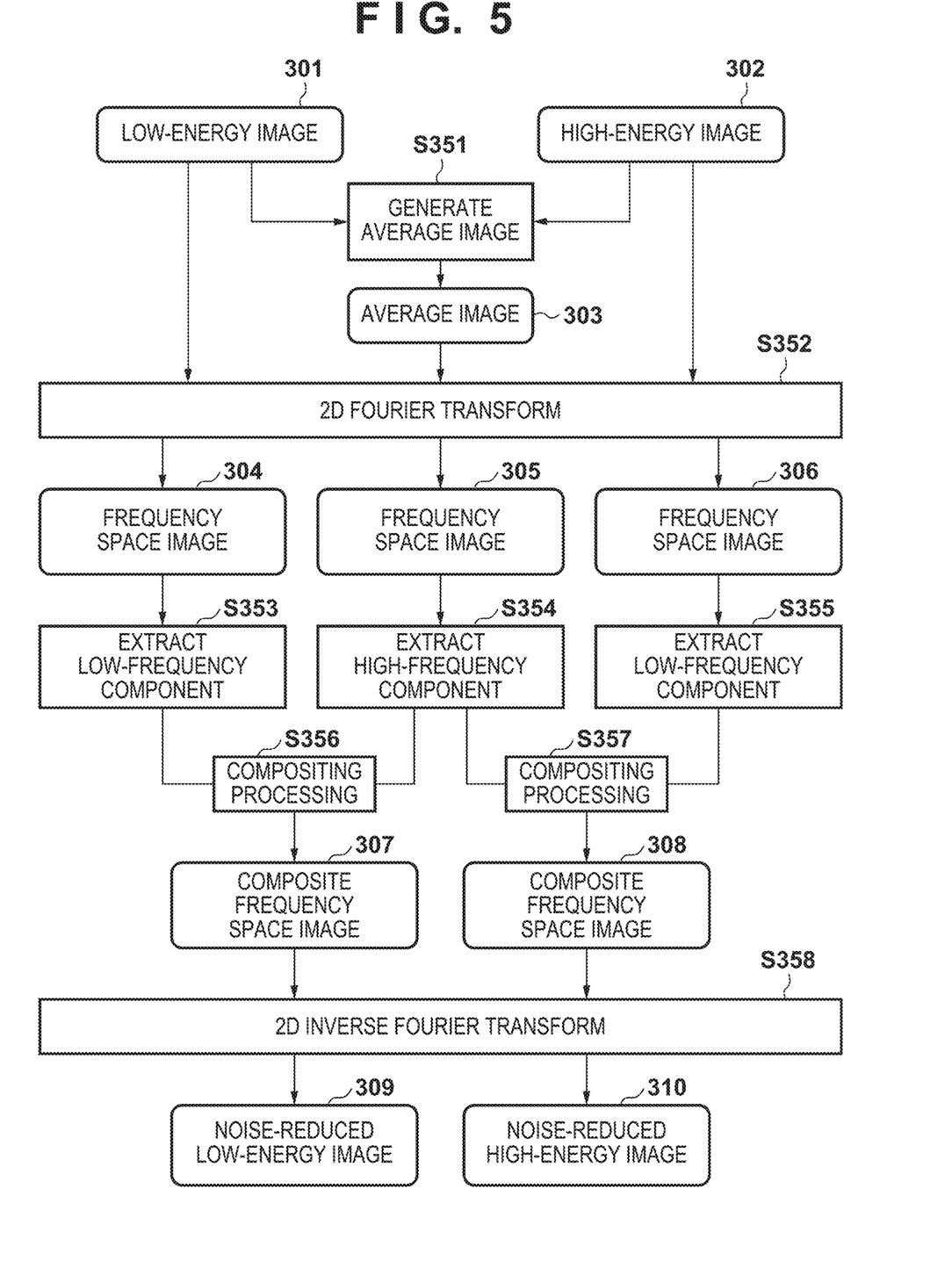
FIG. 5 is a flowchart illustrating image capturing processing according to an embodiment.

First, the average energy of the radiation emitted is changed, and a low-energy image 301 captured at a relatively low radiation energy and a high-energy image 302 captured at a relatively high radiation energy are captured. Here, to change the average energy of the radiation, it is common to change a tube voltage applied to a radiation tube of the radiation generation device 101. Otherwise, in the case of X-rays, for example, the fact that X-rays emitted from an X-ray tube are white light with a mixture of continuous energy photons may be used. In this case, a filter using a metal such as aluminum or copper may be used to absorb more low-energy X-ray photons than high-energy x-rays, or the two may be combined to change the average energy of the X-rays.

In S351, the generating unit 132 obtains an average image 303 having reduced quantum noise by averaging the low-energy image 301 and the high-energy image 302 which have been collected. Because averaging the digital values of the two images includes adding the two images, the average image 303 is an example of the processed image (an image having reduced quantum noise) described above. Note that an additive image obtained by adding a plurality of images, or an average image or an additive image obtained by weighting each image, for example, can be used as the processed image having reduced quantum noise. Here, the weighting is performed on the basis of at least one of, for example, a signal strength (pixel value and density) and a noise strength (variance) in the plurality of images. For example, it is conceivable to add a greater weight as the signal strength increases, or add a smaller weight as the noise strength increases.

To prevent the occurrence of inconsistencies in the compositing of signals in a frequency space, which is performed later, it is desirable that the signal strength of the average image 303 be equivalent to the signal strengths of the low-energy image 301 and the high-energy image 302 on which the average image 303 is based. Accordingly, for example, the low-energy image 301 and the high-energy image 302 may be changed so that the signal strengths thereof are equivalent values, before the average image is generated. Alternatively, the signal strength of the average image 303 may be changed to match the low-energy image 301 and the high-energy image 302, respectively.

Next, in S352 to S355, the compositing unit 133 extracts a low-frequency component image from a frequency space image of one of the images (the low-energy image 301 and the high-energy image 302), and extracts a high-frequency component image from a frequency space image of the processed image (the average image 303). Then, in S356 to S357, the compositing unit 133 obtains the composite image by compositing the low-frequency component image and the high-frequency component image, and converting the result to an image in real space. This will be described in detail below.

In S352, the compositing unit 133 converts each of the low-energy image 301, the high-energy image 302, and the average image 303 into the frequency space using a 2D Fourier transform, and obtains frequency space images 304, 305, and 306 as a result. In S353, the compositing unit 133 obtains the low-frequency component image by extracting a low-frequency component from the frequency space image 305 obtained by converting the low-energy image 301 into the frequency space. In S354, the compositing unit 133 obtains the high-frequency component image by extracting a high-frequency component from the frequency space image 306 obtained by converting the average image 303 into the frequency space. Then, in S356, the compositing unit 133 generates a composite frequency space image 307 by compositing the low-frequency component image and the high-frequency component image extracted in S353 and S354 without gaps. In S358, the compositing unit 133 performs a 2D inverse Fourier transform on the composite frequency space image 307. By returning the composite frequency space image 307 to a real image space in this manner, a noise-reduced low-energy image 309, in which quantum noise is reduced and the contrast of the low-energy image 301 is strongly reflected, is generated.

Likewise, in S355, the compositing unit 133 obtains the low-frequency component image by extracting a low-frequency component from the frequency space image 306 obtained by converting the high-energy image 302 into the frequency space. Then, in S357, the compositing unit 133 generates a composite frequency space image 308 by compositing the low-frequency component image extracted in S355 and the high-frequency component image extracted in S354 without gaps. In S358, the compositing unit 133 performs a 2D inverse Fourier transform on the composite frequency space image 308. By returning the composite frequency space image 308 to a real image space in this manner, a noise-reduced high-energy image 310, in which quantum noise is reduced and the contrast of the high-energy image 302 is strongly reflected, is generated.

The strength of quantum noise in the average image is reduced to $1/\sqrt{2}$ when the number of radiation photons per image is set to B, as indicated in [Equation 2]. It is assumed that ideally, the noise-reduced low-energy image 309 and the noise-reduced high-energy image 310 are converted to quantum noise strengths equivalent to that of the average image. In this case, the target quantum noise strength in the noise-reduced low-energy image 309 and the noise-reduced high-energy image 310 can be achieved with ½ the radiation photon number in each, taking [Equation 1] into account. Accordingly, using the processing illustrated in FIG. 5, when a plurality of radiographic images are captured for time-resolved spectral imaging, the strength of the quantum noise in each image will be dependent on the total number of visible light photons. As such, even if the dose when capturing a plurality of radiographic images is reduced, the strength of the quantum noise in each image can be maintained at the desired strength as long as the total number of visible light photons in a series of a plurality of radiographic images is equal to the number of visible light photons at which the target quantum noise strength is achieved. As a result, even when it is necessary to capture a plurality of images of the same area for spectral imaging, it is only necessary to maintain the number of visible light photons as the total for the plurality of images, which makes it possible to reduce the exposure for each image.

Figure 6:
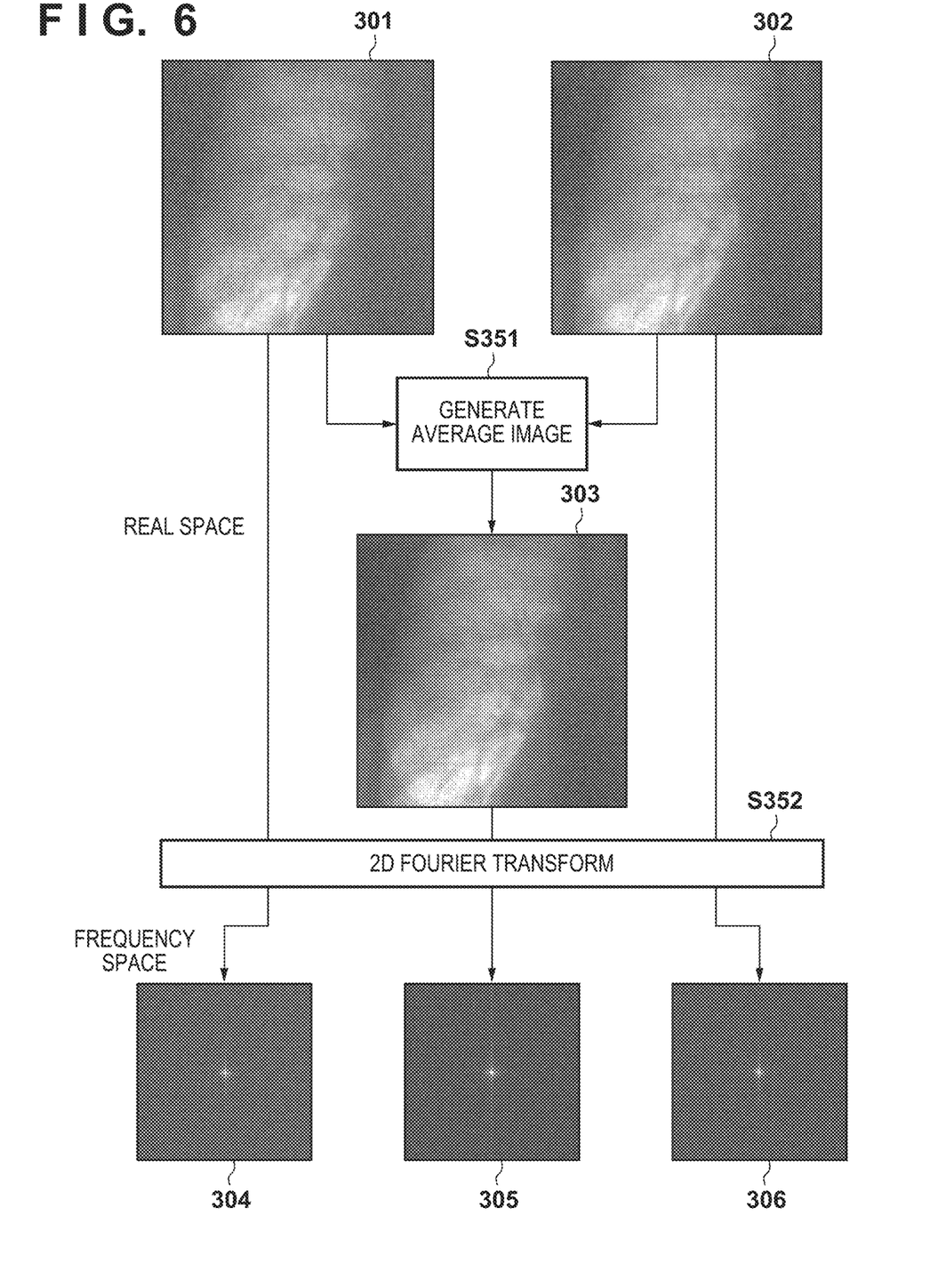
FIG. 6 is a diagram illustrating processing for converting from real space to a frequency space.

An example of the actual processing will be described below with reference to FIG. 6 and FIG. 7. FIG. 6 is a diagram illustrating an example of processing for conversion from the real space to the frequency space, and FIG. 7 is a diagram illustrating an example of processing for conversion from the frequency space to the real space.

In FIG. 6, the generating unit 132 generates the average image 303 of the low-energy image 301 and the high-energy image 302 (S351). Then, the compositing unit 133 performs a 2D Fourier transform on the low-energy image 301, the high-energy image 302, and the average image 303 (S352). The frequency space image 304 of the low-energy image 301, the frequency space image 305 of the average image 303, and the frequency space image 306 of the high-energy image 302 are obtained as a result.

Figure 7:
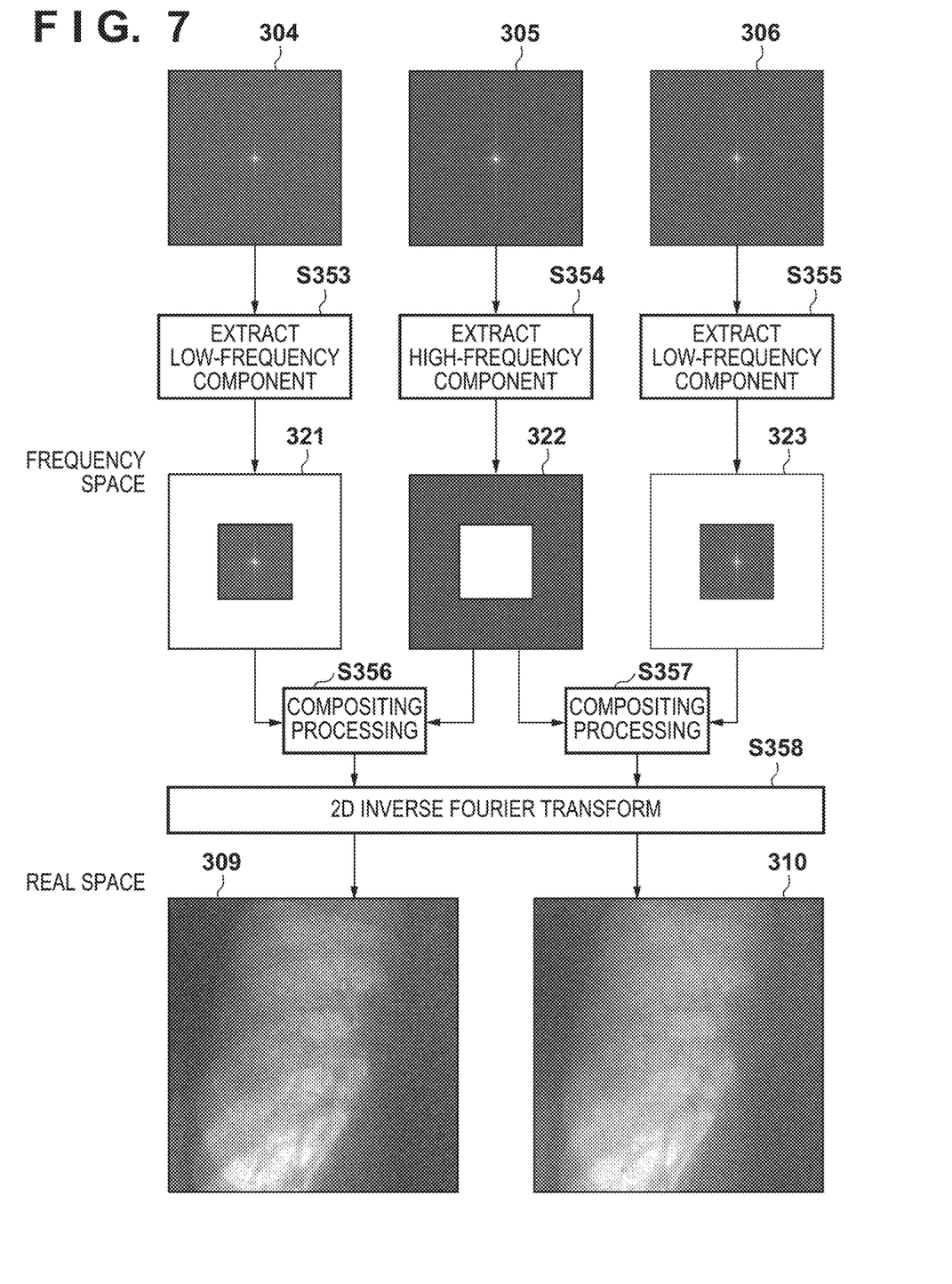
FIG. 7 is a diagram illustrating processing for converting from a frequency space to real space.

In FIG. 7, the compositing unit 133 creates a low-frequency component image 321 by extracting a low-frequency component from the frequency space image 304 of the low-energy image 301 (S353). Likewise, the compositing unit 133 creates a low-frequency component image 323 by extracting a low-frequency component from the frequency space image 306 of the high-energy image 302 (S355). Additionally, the compositing unit 133 creates a high-frequency component image 322 by extracting a high-frequency component from the frequency space image 305 of the average image 303 (S354).

The compositing unit 133 generates the composite frequency space image 307 (FIG. 5) by compositing the low-frequency component image 321 and the high-frequency component image 322 so that there is no overlap (S356). Then, by performing a 2D inverse Fourier transform on the composite frequency space image 307 (S358) and returning the image to an image in real space, the compositing unit 133 generates the noise-reduced low-energy image 309. Additionally, the compositing unit 133 generates the composite frequency space image 308 (FIG. 5) by compositing the low-frequency component image 323 and the high-frequency component image 322 so that there is no overlap (S357). Then, by performing a 2D inverse Fourier transform on the composite frequency space image 308 (S358) and returning the image to an image in real space, the compositing unit 133 generates the noise-reduced high-energy image 310.

Furthermore, the control computer 103 generates a spectral imaging image using the noise-reduced low-energy image 309 and the noise-reduced high-energy image 310. The signal of each pixel (output data) following the 2D inverse Fourier transform 358 on the composite frequency space images 307 and 308 has had its value changed in the composite frequency space image 307, and thus the complex numbers obtained from the 2D Fourier transform (S352) remain as-is. The control computer 103 ultimately finds the absolute values of these complex numbers and takes those values as the pixel values.

Note that the above-described processing may be realized by a computer (the processor 121) executing a predetermined program, or all or part of the processing may be realized using dedicated hardware (circuitry).

Figure 8A:
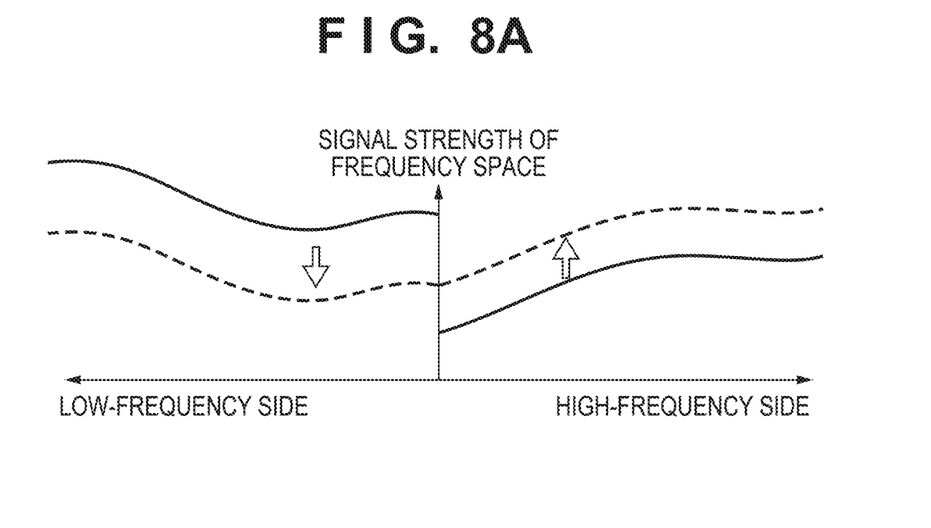
FIG. 8A is a diagram illustrating processing performed when compositing images.
Figure 8B:
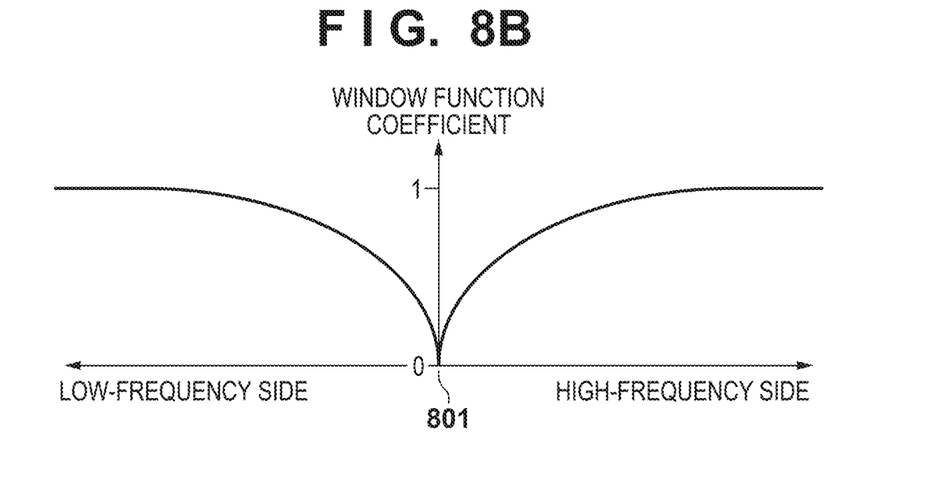
FIG. 8B is a diagram illustrating processing performed when compositing images.

Note also that in the process of generating the composite frequency space images 307 and 308 (S356, S357), the ratio at which the high-frequency component and the low-frequency component are composited may be varied for the purpose of preventing moiré, maintaining contrast information, adjusting the strength of noise, and the like. For example, as illustrated in FIG. 8A, the ratio at which the low-frequency component and/or the high-frequency component is/are composited may be set so that the signal values of both images are equal at a boundary between the low-frequency component image and the high-frequency component image. Additionally, a window function may be introduced to prevent moiré when generating the composite frequency space images 307 and 308 through S356 and S357. For example, a window function is applied so that the respective signal values of the low-frequency component and the high-frequency component decrease as the distance to the boundary between the low-frequency component image and the high-frequency component image decreases and the signal values reach zero at the position of the boundary. FIG. 8B illustrates an example of the window function. The window function in FIG. 8B has a coefficient of 0 at a boundary position 801, which is a part where the high-frequency component and the low-frequency component connect.

Although the shape of a figure forming the boundary between the low-frequency component images 321 and 323 and the high-frequency component image 322 is a square in the embodiment described above, a rectangle, a regular circle, an ellipse, or another shape may be used instead. The area of the figure forming the boundary may be variable as well. Furthermore, a user may be capable of setting the boundary between the low-frequency component and the high-frequency component, and in this case, the user may select the shape of the figure as described above, set the area, and so on.

Additionally, although a 2D Fourier transform (S352) and a 2D inverse Fourier transform (S358) are used as the processing for converting between real space and the frequency space, the processing is not limited thereto. For example, frequency processing aside from a Fourier transform, such as a wavelet transform, may be used to separate and composite the high-frequency component and the low-frequency component.

Additionally, rather than using the frequency space, the noise-reduced low-energy image 309 and the noise-reduced high-energy image 310 may be obtained through a computation method in real space. In other words, the compositing unit 133 generates a first image in which the low-frequency component of one image in the real space (e.g., the low-energy image 301 or the high-energy image 302) is enhanced. Additionally, the compositing unit 133 generates a second image in which the high-frequency component of the processed image in the real space (e.g., the average image 303) is enhanced. Then, by compositing the first image and the second image, the compositing unit 133 obtains a composite image in which quantum noise is reduced while maintaining the contrast (the noise-reduced low-energy image 309 and the noise-reduced high-energy image 310).

For example, rather than performing the 2D Fourier transform and the 2D inverse Fourier transform, the compositing unit 133 enhances the low-frequency component by reducing the high-frequency components in the low-energy image 301 and the high-energy image 302 using a moving average or similar technique. The compositing unit 133 enhances the high-frequency component of the average image 303 using a Laplacian or similar technique. The compositing unit 133 obtains the noise-reduced low-energy image 309 by compositing the image in which the low-frequency component of the low-energy image 301 is enhanced, and the image in which the high-frequency component of the average image 303 is enhanced, obtained in this manner. Likewise, the compositing unit 133 obtains the noise-reduced high-energy image 310 by compositing the image in which the low-frequency component of the high-energy image 302 is enhanced and the image in which the high-frequency component of the average image 303 is enhanced. In this manner, four arithmetic operations such as simple addition may be used to composite the images, or logarithmic processing may be used.

Furthermore, although two images having different average energies are used to generate spectral imaging images in the embodiment described above, the configuration is not limited thereto, and the above-described processing can also be applied when three or more images are used. In other words, the quantum noise of each image can be reduced by compositing images using a high-frequency component of an average image created from N (N≥2) images having different average energies and a low-frequency component of each of the N images.

As described above, according to the embodiment, even if a plurality of radiographic images are captured to obtain a spectral imaging image that separates the radiation energy, an image having a similar quantum noise can be provided at a radiation dose equivalent to that of a normal single shot.

According to the present disclosure, noise in an image can be reduced while suppressing a radiation exposure dose to an examinee when capturing a plurality of radiographic images.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
    at least one of (a) one or more processors connected to one or more memories storing a program including instructions executed by the one or more processors and (b) circuitry, configured to function to generate a composite image by compositing (a) a first image obtained by enhancing a low-frequency component of one image among a plurality of images corresponding to a plurality of energies different from each other and (b) a second image obtained by enhancing a high-frequency component of a processed image obtained by compositing the plurality of images.

2. The image processing apparatus according to claim 1, wherein the processed image is obtained by adding the plurality of images.

3. The image processing apparatus according to claim 1, wherein the processed image is obtained by adding the plurality of images after performing weighting on the basis of at least one of a strength of a signal and a strength of noise in the plurality of images.

4. The image processing apparatus according to claim 1, wherein the composite image is generated by extracting a low-frequency component image from a frequency space image of the one image, extracting a high-frequency component image from a frequency space image of the processed image, compositing the low-frequency component image and the high-frequency component image, and converting a result of the compositing into an image in real space.

5. The image processing apparatus according to claim 4, wherein the one image and the processed image are converted into respective frequency space images using a Fourier transform or a wavelet transform.

6. The image processing apparatus according to claim 4, wherein the at least one of (a) one or more processors connected to one or more memories storing a program including instructions executed by the one or more processors and (b) circuitry further functions to change a ratio used for compositing the low-frequency component image and the high-frequency component image.

7. The image processing apparatus according to claim 4, wherein a boundary between the high-frequency component and the low-frequency component is set to the low-frequency component image of the one image and the high-frequency component image of the processed image.

8. The image processing apparatus according to claim 4, wherein a window function is applied to a part where the high-frequency component image and the low-frequency component image connect.

9. The image processing apparatus according to claim 1, wherein the composite image is obtained by:
    generating a first image in which a low-frequency component of the one image in real space is enhanced;
    generating a second image in which a high-frequency component of the processed image in real space is enhanced; and
    compositing the first image and the second image.

10. The image processing apparatus according to claim 9, wherein the first image is generated by reducing high-frequency components of the one image.

11. The image processing apparatus according to claim 9, wherein the second image is generated by enhancing the high-frequency component using a Laplacian on the processed image.

12. The image processing apparatus according to claim 9, wherein the composite image is generated by simple addition of the first image and the second image.

13. The image processing apparatus according to claim 9, wherein the composite image is generated by compositing the first image and the second image using a logarithm of pixel values of the first image and the second image.

14. A control method of an image processing apparatus, the method comprising:
    generating a composite image by compositing (a) a first image obtained by enhancing a low-frequency component of one image among a plurality of images corresponding to a plurality of energies different from each other and (b) a second image obtained by enhancing a high-frequency component of a processed image obtained by compositing the plurality of images.

15. A non-transitory computer-readable storage medium storing a program that causes a computer to execute a control method of an image processing apparatus, the method comprising:
    generating a composite image by compositing (a) a first image obtained by enhancing a low-frequency component of one image among a plurality of images corresponding to a plurality of energies different from each other and (b) a second image obtained by enhancing a high-frequency component of a processed image obtained by compositing the plurality of images.

16. The image processing apparatus according to claim 1, wherein the at least one of (a) one or more processors connected to one or more memories storing a program including instructions executed by the one or more processors and (b) circuitry further functions to generate a spectral imaging image using a plurality of composite images obtained by generating the composite image for each of the plurality of images.

17. The image processing apparatus according to claim 10, wherein the first image is generated by enhancing the low-frequency component by calculating a moving average of the one image.

* * * * *